(12) United States Patent
Andersson et al.

(10) Patent No.: US 6,244,118 B1
(45) Date of Patent: Jun. 12, 2001

(54) SAMPLING APPARATUS

(75) Inventors: Martin Andersson, Lund; Ingela N Björn, Göteborg; Staffan Folestad, Västra Frölunda, all of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/230,991

(22) PCT Filed: Dec. 23, 1998

(86) PCT No.: PCT/SE98/02451

§ 371 Date: Feb. 5, 1999

§ 102(e) Date: Feb. 5, 1999

(87) PCT Pub. No.: WO99/32872

PCT Pub. Date: Jul. 1, 1999

(30) Foreign Application Priority Data

Dec. 23, 1997 (SE) .................................................. 9704873

(51) Int. Cl.$^7$ ........................................................ G01N 1/00
(52) U.S. Cl. ...................................... 73/863.52; 73/864.81
(58) Field of Search ........................... 73/863.51–863.54, 73/863.81, 863.82, 863.85, 864.81, 865.5, 863.52; 250/341.1, 341.2, 341.7, 341.8, 358.1, 360.1; 356/438, 440, 244

(56) References Cited

U.S. PATENT DOCUMENTS

| | | |
|---|---|---|
| 4,640,614 | 2/1987 | Roberts et al. . |
| 5,750,996 | * 5/1998 | Drennen, III et al. ........... 250/341.2 |
| 5,992,245 | * 11/1999 | Takei et al. .................... 73/865.5 |

FOREIGN PATENT DOCUMENTS

| | | |
|---|---|---|
| 3444013 | 6/1985 | (DE) . |
| 0724145 | 7/1996 | (EP) . |
| WO89/10548 | 11/1989 | (WO) . |
| WO93/23731 | 5/1993 | (WO) . |
| WO96/09528 | 3/1996 | (WO) . |
| WO96/12174 | 4/1996 | (WO) . |
| WO96/24835 | 8/1996 | (WO) . |
| WO99/32872 | 1/1999 | (WO) . |

* cited by examiner

Primary Examiner—Robert Raevis
(74) Attorney, Agent, or Firm—White & Case LLP

(57) ABSTRACT

An apparatus for use in and a method of sampling material on-line in a process system, comprising: a sample collector (1) including a wall member (8) of fixed position on which a sample of material is in use collected; a measuring device (3) for taking measurements from a collected sample; and sample displacing means for displacing the collected sample from the sample collector (1) so that the sample collector (1) can receive a new sample of material.

35 Claims, 3 Drawing Sheets

SAMPLING APPARATUS

The present invention relates to an apparatus for and a method of sampling material in a process system, in particular the on-line sampling of a flow of a liquid or powder.

Traditionally, a sample of material would have been removed during processing from a process system and then analyzed. It will be appreciated that techniques requiring the removal of material from a process system for separate analysis are both labor-intensive and time consuming.

More recently, techniques have been developed which allow material to be analyzed on-line. WO-A-96/12174 discloses an apparatus for the on-line analysis of material in a process system, specifically a reaction vessel. This apparatus comprises a probe, which is located in the reaction vessel and includes a chamber having openings through which material continuously passes, and optical measurement means for analyzing the material passing through the chamber. WO-A-96/24835 discloses an apparatus for the on-line analysis of material in a process system, specifically a tubular section. This apparatus comprises a tube having opposed transparent windows, a light source adjacent one window and a photo-detector adjacent the other window, whereby the composition of the material passing the windows is determined by the signals generated by the photo-detector. Whilst these on-line techniques are less labor-intensive and allow for a more rapid analysis of material, such techniques still exhibit a number of problems. Notably, where a probe is used to analyze a flow of material, it is often difficult to locate the probe in a region of the material which flows continuously and steadily. In fact, it is commonly found that the probe will be located in a region of the material which has a pulsed flow or is indeed stationary. It is also difficult to ensure that the probe is continuously surrounded by fresh material so that the on-going measurement is truly representative of the entire bulk of material. For many reasons, in these prior art techniques the same material can remain next to the probe which leads to the analysis throughout the process cycle as characterizing the entire bulk of material as having the same composition when in fact the position could be quite different.

It is thus a general aim of the present invention to provide an apparatus for and a method of periodically sampling material on-line which is representative of the entire bulk of material from which samples are taken.

It is a particular aim of the present invention to provide a sampling apparatus which ensures a stable interface between the material to be sampled and the measuring device. Where a flow of material is to be sampled, it is desirable to present a stationary sample to the measuring device.

A further aim of the present invention is to provide a sampling apparatus which allows material to be sampled and replaced with new material in a quick and efficient manner.

Accordingly, the present invention provides an apparatus for use in sampling material on-line in a process system, comprising: a sample collector including an upwardly-facing wall member of fixed position on which a sample of material is in use collected; a measuring device for talking measurements from a collected sample; and sample displacing means for displacing the collected sample from the sample collector so that the sample collector can receive a new sample of material. In preferred embodiments the process system is one of a process vessel or a tubular section.

By virtue of the configuration of the sampling apparatus of the present invention, a relatively simple construction is provided which avoids the need to remove material from the process system and allows for a stationary sample to be presented to the measuring device. The construction also allows for a collected sample from which measurements have been taken to be replaced both simply and rapidly. In addition, the configuration of the sampling apparatus of the present invention is such that it is in effect self-cleaning, thereby minimizing the down-time of the process system from which material is being sampled. Moreover, the sampling apparatus of the present invention allows for the use of any kind of measuring device which utilizes electromagnetic radiation.

In one embodiment the sample displacing means comprises a pressurized gas supply which in use is actuated to displace the collected sample.

As will be appreciated, this embodiment of the sampling apparatus of the present invention exhibits the particular advantage that sampling is achieved without requiring any moving parts or requiring the apparatus to introduce components into the material to be sampled which are electrically operated, thereby minimizing the risk of an explosion.

Preferably, the measuring device is non-destructive or partially destructive.

In one embodiment the measuring device is a spectroscopic measuring device and can be a reflectance, transflectance or transmission device. Preferably, the spectroscopic measuring device is one of an emission, absorbtion or scattering device. In preferred embodiments the spectroscopic measuring device is an x-ray spectrophotometer, an ultra-violet (UV) spectrophotometer, a visible (VIS) spectrophotometer, an infra-red (IR) spectrophotometer, a near infra-red (NIR) spectrophotometer, a raman spectrophotometer, a microwave spectrophotometer or a nuclear magnetic resonance (NMR) spectrophotometer.

In another embodiment the measuring device is a polarimeter.

In a preferred embodiment the measuring device includes a measurement probe and the sample collector is attached to the distal end of the measurement probe such as to be movable within the process system. This configuration is particularly useful when representative samples are not to be found adjacent the wall of a process system or if homogeneity is to be monitored at different locations within a process system.

In a preferred embodiment the sample collector is connected to a heating/cooling means so as to provide for temperature stabilization of the sample collector. Temperature stabilization can provide more reliable measurements where the measuring device is sensitive to variations in temperature or where, for example, the material to be sampled is a liquid which tends to boil, with the gas bubbles generated adversely affecting the measurement The present invention also provides a method of sampling material on-line in a process system, comprising the steps of: collecting a sample of material in a sample collector, the sample collector including an upwardly-facing wall member of fixed position on which a sample of material is collected; taking measurements from the collected sample; and displacing the collected sample from the sample collector.

In a preferred embodiment the collected sample is displaced from the sample collector using a pressurized gas supply.

The present invention finds particular application in monitoring the characteristics, for example compositional changes, of pharmaceutical compositions typically in the form of powders, granules, pellets and tablets during preparation in fluidized beds. However, it will be appreciated that the present invention can equally be applied to other processes within the pharmaceutical industry, and indeed in non-pharmaceutical processes. Other processes to which the present invention can be applied are typically blender systems, powder transport devices, spray granulators, spray dryers and mixing/separation systems.

Preferred embodiments of the present invention will now be described hereinbelow by way of example only with reference to the accompanying drawings, in which:

FIG. 1 schematically illustrates a sampling apparatus in accordance with a first embodiment of the present invention incorporated in a process vessel;

Figure 4:
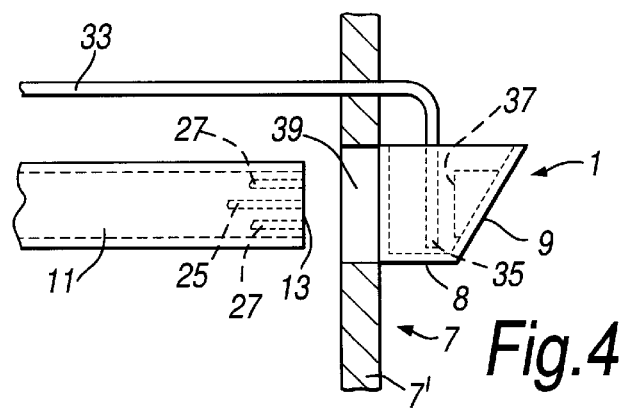
Figure 5:
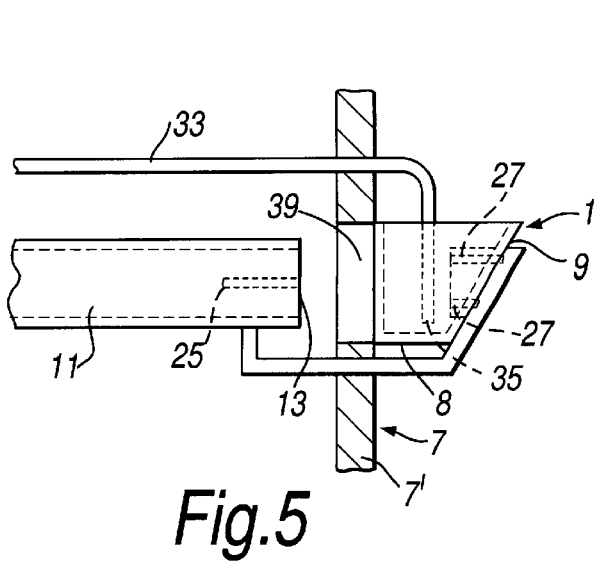
Figure 8:
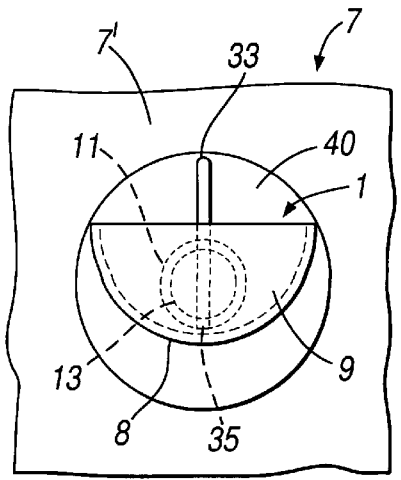
Figure 6:
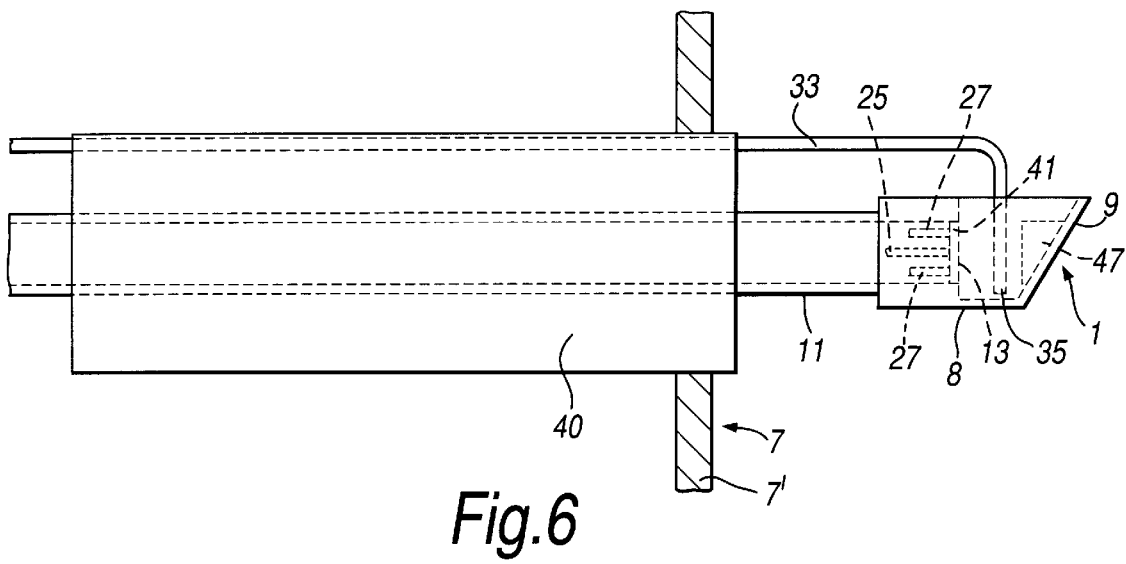
Figure 7:
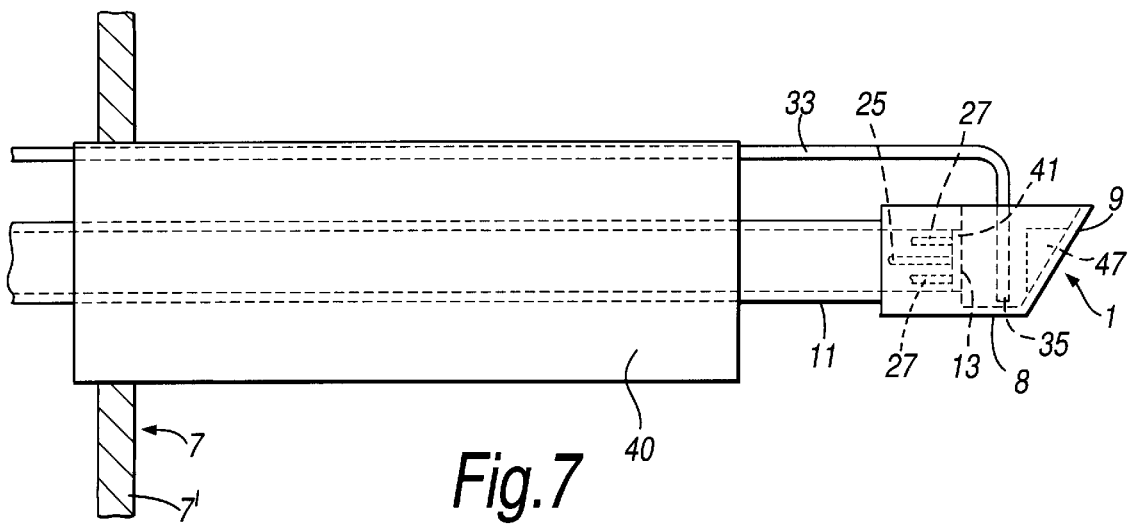

FIG. 4. schematically illustrates part of a sampling apparatus in accordance with a second embodiment of the present invention at the peripheral wall of a process vessel;

FIG. 5 schematically illustrates part of a sampling apparatus in accordance with a third embodiment of the present invention at the peripheral wall of a process vessel;

FIG. 6 schematically illustrates part of a sampling apparatus in accordance with a fourth embodiment of the present invention at the peripheral wall of a process vessel, with the sample collector located in a first position adjacent the peripheral wall of the process vessel;

FIG. 7 schematically illustrates the part of the sampling apparatus of FIG. 6, with the sample collector located in a second position distant from the peripheral wall of the process vessel; and FIG. 8 illustrates a front view of the sampling apparatus of FIG. 6.

Figure 1:
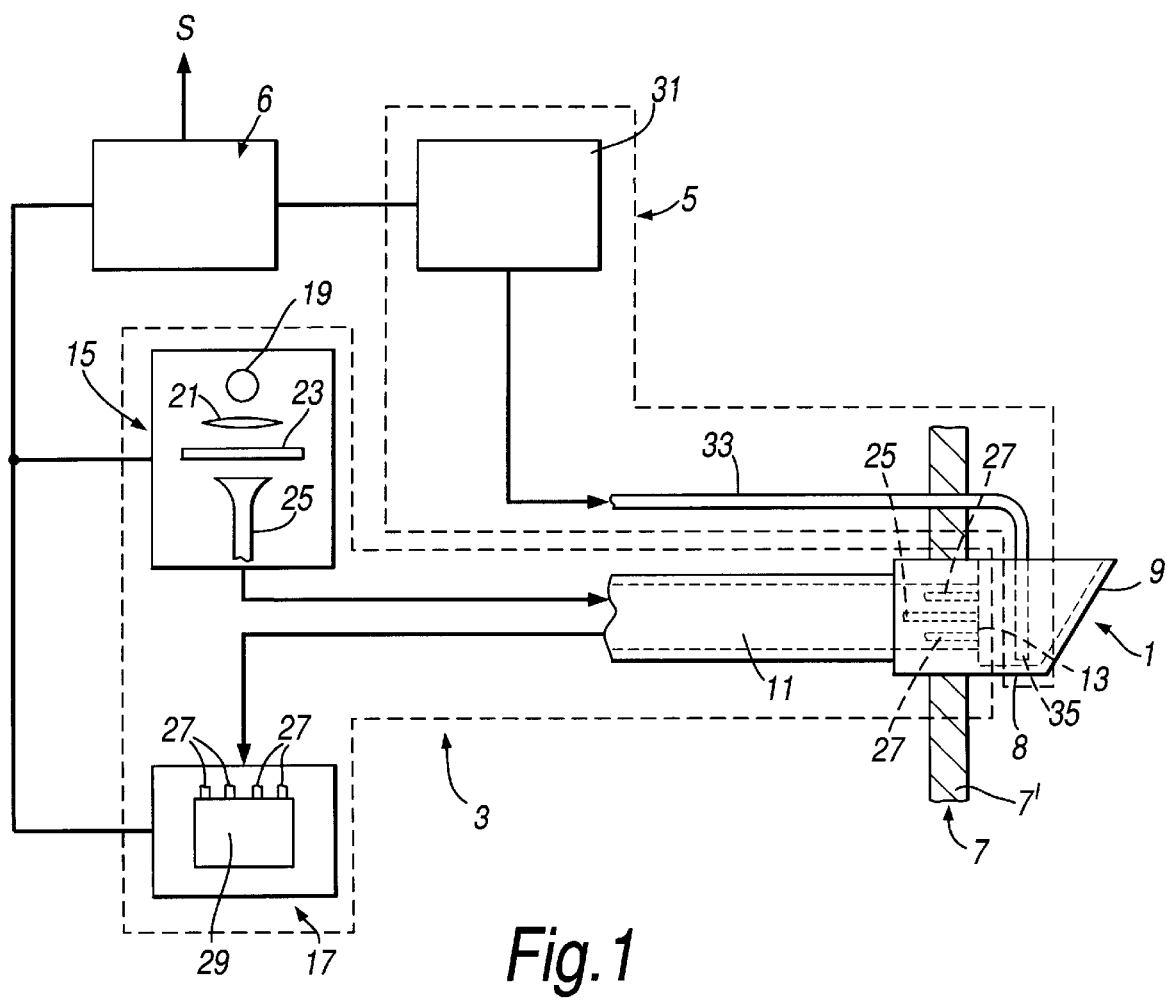
Figure 2:
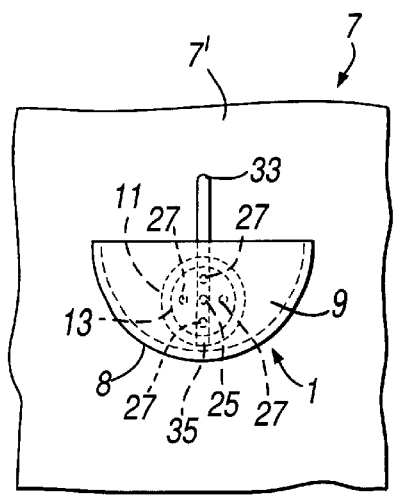
FIG. 2 illustrates a front view of the sampling apparatus of FIG. 1.

FIGS. 1 and 2 illustrate a sampling apparatus in accordance with a first embodiment of the present invention.

The sampling apparatus comprises a sample collector 1 for collecting a sample of material, a measuring device 3 for taking measurements from a collected sample, a sample displacement device 5 for displacing a collected sample from the sample collector 1 and a controller 6. The operation of each of the sample collector 1, the measuring device 3 and the sample displacement device 5 is performed under the control of the controller 6, typically a computer or a programmable logic controller (PLC), as will be described in more detail hereinbelow.

The sample collector 1 is fixed to an inner surface of the peripheral wall 7' of a process vessel 7. The sample collector 1, in this embodiment an open-topped chamber, includes an arcuate wall member 8 on which powder is in use collected and a front wall member 9 which tapers upwardly and outwardly for assisting in guiding material thereinto.

The measuring device 3 includes a measurement probe 11, in this embodiment a near infra-red reflectance probe, which extends through the peripheral wall 7' of the process vessel 7 such that the distal end 13 of the measurement probe 11, through which radiation is emitted and received, is directed into the sample collector 1. In this manner measurements can be taken from a sample of material collected in the sample collector 1.

The measuring device 3 further includes a radiation generating unit 15 for generating electromagnetic radiation and a detector unit 17 for detecting the radiation difffusely reflected by a collected sample.

In this embodiment the radiation generating unit 15 comprises in the following order: a radiation source 19, preferably a broad spectrum visible to infra-red source, such as a tungsten-halogen lamp, which emits radiation in the near infra-red interval of from 400 to 2500 nm, a focusing lens 21, a filter arrangement 23 and at least one fiber cable 25 for leading the focused and filtered radiation to distal end 13 of the measurement probe 11. In this embodiment the filter arrangement 23 comprises a plurality of filters, each allowing the passage of radiation of a respective single frequency or frequency band. In other embodiments a monochromator or a spectrometer of Fourier transform kind can be used instead of the filter arrangement 23.

In this embodiment the detector unit 17 comprises in the following order: an array of fiber cables 27, whose distal ends are arranged around the distal end of the at least one fiber cable 25 which supplies radiation to a collected sample, and a detector 29 connected to the fiber cables 27. The detector 29 is preferably an array detector such as a CMOS chip, a CCD chip or a focal plane array. The distal ends of the fiber cables 27 are preferably spaced from the distal end of the at least one fiber cable 25 in order to minimize the effect of specular reflection or stray energy reaching the fiber cables 27. In use, the detector 29 will produce signals S depending upon the composition of the sampled material and the frequency of the supplied radiation. These signals S are then amplified, filtered and digitized so as to be available for further processing. The processed signals can be used to perform real-time or subsequent analysis. Alternatively or additionally, the processed signals can be used for process control.

The sample displacement device 5 comprises a high-pressure gas source 31, in this embodiment an air compressor, and a small bore tube 33 which extends from the high-pressure gas source 31 through the peripheral wall 7' of the process vessel 7 to the sample collector 1. The distal end 35 of the small bore tube 33 is directed downwardly into the sample collector 1 such that, when pressurized gas is delivered therethrough, material resident in the sample collector 1 is displaced, that is, blown out, whereupon a new sample may be collected from which measurements can be taken. By arranging the distal end 35 of the small bore tube 33 so as to be downwardly-directed the risk of material entering the small bore tube 33 is minimized. In this embodiment the distal end 35 of the small bore tube 33 is disposed adjacent the lowermost part of the upper surface of the arcuate wall member 8 of the sample collector 1. Typically, the pressurized gas is at a pressure of the order of 1 bar and is supplied for about 0.1 seconds. The pressure and the duration of the pressure pulse which has to be used will vary depending upon the material being sampled, but these parameters can be determined by routine experimentation.

Figure 3:
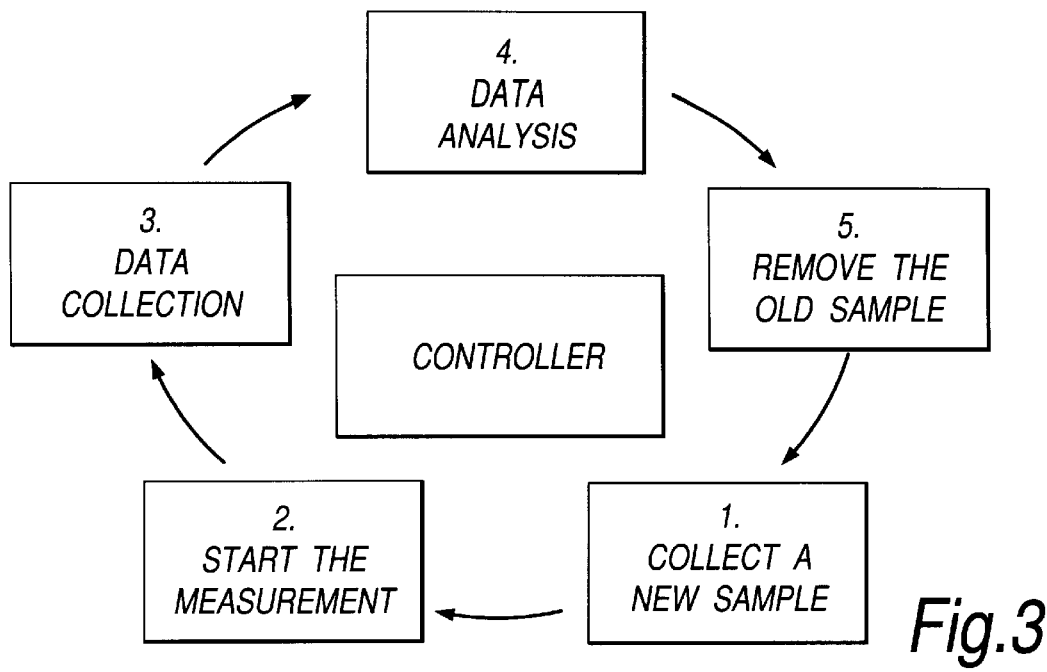
FIG. 3 illustrates a flow chart of a method of sampling material in accordance with the present invention.

The sequence of operation of the sampling apparatus of FIGS. 1 and 2 is schematically illustrated in FIG. 3. In use, a sample is first collected in the sample collector 1 (Step 1). The sampling apparatus is then initiated to start measurement either automatically or by the intervention of an operator (Step 2). Under the control of the controller 6, measurements are then taken from the sample collected in the sample collector 1 using the measuring device 3 to generate data corresponding to the received radiation (Step 3). As the data is generated it is then either analyzed in real time or stored for subsequent analysis (Step 4), with the resulting information optionally being used for process control. After all of the required measurements have been taken from the sample, the controller 6 then actuates the sample displacement device 5 which in this embodiment actuates the high-pressure gas source 31, whereupon pressurized gas is delivered through the small bore tube 33 into the sample collector 1 and the sample resident in the sample collector 1 is displaced such that a new sample can be collected (Step 5). The sampling method can then be repeated to take measurements from another sample of material.

FIGS. 4 to 8 respectively illustrate sampling apparatuses or parts thereof in accordance with second to fourth embodiments of the present invention. These sampling apparatuses are quite similar structurally and operate in the same manner as the sampling apparatus in accordance with the first embodiment of the present invention as described hereinabove in relation to FIGS. 1 to 3. Hence, in order not to duplicate description unnecessarily, only the structural differences of the sampling apparatuses of these further embodiments will be described. It will of course be appreciated that features of the sampling apparatuses of these further embodiments and the sampling apparatus of the embodiment of FIGS. 1 and 2 can be used in conjunction with one another.

FIG. 4 illustrates part of a sampling apparatus in accordance with a second embodiment of the present invention and incorporates a transflective measuring device. This sampling apparatus differs from that of the first embodiment of the present invention in that the measurement probe 11 does not extend into the sample collector 1 and in that a reflective surface 37, typically a mirrored surface, is provided on the inner side of the sample collector 1 opposed to the path of the radiation supplied by the at least one fiber cable 25. In order to allow transmission of radiation from the measurement probe 11 into the sample collector 1, the peripheral wall 7' of the process vessel 7 is provided with a window 39 which is transparent or at least translucent to the radiation employed by the measuring device 3. In use, radiation provided by the at least one fiber cable 25 passes through a sample of material collected in the sample collector 1 and is reflected back to the fiber cables 27 by the reflective surface 37.

FIG. 5 illustrates part of a sampling apparatus in accordance with a third embodiment of the present invention and incorporates a transmissive measuring device. This sampling apparatus differs from that of the first embodiment of the present invention in that the measurement probe 11 does not extend into the sample collector 1 and in that the distal ends of the fiber cables 27 are located at the inner side of the sample collector 1 opposed to the path of the radiation supplied by the at least one fiber cable 25. Similarly to the embodiment of FIG. 4, in order to allow transmission of radiation from the measurement probe 11 into the sample collector 1, the peripheral wall 7' of the process vessel 7 is provided with a window 39 which is transparent or at least translucent to the radiation employed by the measuring device 3. In use, radiation provided by the at least one fiber cable 25 passes through a sample of material collected in the sample collector 1 and is detected by the fiber cables 27.

FIGS. 6 to 8 illustrate part of a sampling apparatus in accordance with a fourth embodiment of the present invention. This sampling apparatus differs from that of the first embodiment of the present invention in that the sample collector 1 is mounted to the distal end 13 of the measurement probe 11 and in that the measurement probe 11 and the small bore tube 33 of the sample displacement device 5 are provided in a slide body 40 which is slideably mounted in the wall 7' of the process vessel 7. In this way, the sample collector 1 can be located at a range of positions relative to the wall 7' of the process vessel 7 so as to allow measurements to be taken from samples at those positions. The sampling apparatus further differs from that of the first embodiment of the present invention in that the distal end 13 of the measurement probe 11 includes an element 41 which is transparent or at least translucent to the radiation employed by the measuring device 3 and acts as a means of protection for the fiber cables 25, 27. This sampling apparatus yet further differs from that of the first embodiment of the present invention in that a block of material 47 of known characteristic, such as polystyrene, is provided on the inner side of the sample collector 1 opposed to the path of the radiation supplied by the at least one fiber cable 25. The block 47 serves as a standard which enables the sampling apparatus to be calibrated when the sample collector 1 is empty. In this way, the measurement probe 11 can be calibrated in situ.

Finally, it will be understood by a person skilled in the art that the present invention is not limited to the described embodiments but can be modified in many different ways without departing from the scope of the invention as defined in the appended claims.

What is claimed is:

1. An apparatus for use in sampling material on-line in a process system, comprising:
   a sample collector comprising an open-topped chamber having an arcuate wall member for receiving a sample of material, and a front wall member which is flared upwardly and outwardly;
   a measuring device comprising a measurement probe for taking measurements from a collected sample; and
   sample displacing means for displacing the collected sample from the sample collector so that the sample collector can receive a new sample of material.

2. The apparatus according to claim 1 incorporated in a process system, wherein the sample collector is located within the process system.

3. The apparatus according to claim 2, wherein the sample collector is movable relative to an inner surface of the process vessel.

4. The apparatus according to claim 2, wherein the sample collector is located adjacent an inner surface of the process vessel.

5. The apparatus according to claim 2, wherein the sample collector is fixed to an inner surface of the process vessel.

6. The apparatus according to claim 2, wherein the process system comprises a process vessel.

7. The apparatus according to claim 2, wherein the process system comprises a tubular section.

8. A method of sampling material on-line in a process system, comprising the steps of:
   collecting a sample of material in a sample collector, the sample collector comprising
   an open-topped chamber having an arcuate wall member on which a sample is collected and a front wall member which is flared upwardly and outwardly for receiving a sample in a process vessel of the process system;
   taking measurements from the collected sample with a measuring device comprising a measurement probe which extends into the process vessel; and
   displacing the collected sample from the sample collector.

9. The method according to claim 8, wherein the process system comprises a process vessel.

10. The apparatus according to claim 1, wherein the sample displacing means comprises a pressurized gas supply which is actuated to displace the collected sample when the apparatus is in use.

11. The apparatus according to claim 10, wherein the pressurized gas supply comprises a tube whose distal end is directed at the sample collector.

12. The apparatus according to claim 11, wherein the distal end of the pressurized gas supply tube is located adjacent an upper surface of the sample collector.

13. The apparatus according to claim 12, wherein the distal end of the pressurized gas supply tube is located adjacent a lowermost part of the upper surface of the sample collector.

14. The apparatus according to any one of claims 1, 10, 11, 12, or 13, wherein the measuring device is a polarimeter.

15. The apparatus according to any one of claims 1, 10, 11, 12 or 13, wherein the measuring device is a spectroscopic measuring device.

16. The apparatus according to claim 15, wherein the spectroscopic measuring device is one of a reflectance, transflectance or transmission device.

17. The apparatus according to claim 16, wherein the spectroscopic measuring device comprises an infra-red spectrophotometer.

18. The apparatus according to claim 16, wherein the spectroscopic measuring device comprises a near infra-red spectrophotometer.

19. The apparatus according to claim 16, wherein the spectroscopic measuring device comprises an x-ray spectrophotometer.

20. The apparatus according to claim 16, wherein the spectroscopic measuring device comprises a visible-wavelength spectrophotometer.

21. The apparatus according to claim 16, wherein the spectroscopic measuring device comprises a raman spectrophotometer.

22. The apparatus according to claim 16, wherein the spectroscopic measuring device comprises a microwave spectrophotometer.

23. The apparatus according to claim 16, wherein the spectroscopic measuring device comprises a nuclear magnetic resonance spectrophotometer.

24. The apparatus according to claim 15, wherein the spectroscopic measuring device comprises an infra-red spectrophotometer.

25. The apparatus according to claim 15, wherein the spectroscopic measuring device comprises a near infra-red spectrophotometer.

26. The apparatus according to claim 15, wherein the spectroscopic measuring device comprises an x-ray spectrophotometer.

27. The apparatus according to claim 15, wherein the spectroscopic measuring device comprises a visible-wavelength spectrophotometer.

28. The apparatus according to claim 15, wherein the spectroscopic measuring device comprises a raman spectrophotometer.

29. The apparatus according to claim 15, wherein the spectroscopic measuring device comprises a microwave spectrophotometer.

30. The apparatus according to claim 15, wherein the spectroscopic measuring device comprises a nuclear magnetic resonance spectrophotometer.

31. The apparatus according to any one of claims 2, 6, 7, 3, 4 or 5, wherein the measurement probe extends into the process system and the sample collector is fixed to the distal end of the measurement probe.

32. The apparatus according to any one of claims 2, 6, 7, 3, 4 or 5, wherein the measuring device is located outside the process system and the process system includes at least one window transparent or at least translucent to the radiation used by the measuring device through which measurements of a collected sample are taken.

33. The method according to claim 8, wherein the process system comprises a tubular section.

34. The method according to claim 8, wherein the collected sample is displaced from the sample collector using a pressurized gas.

35. The method according to claim 33 or 34, wherein material is sampled from a flow of material.

\* \* \* \* \*

UNITED STATES PATENT AND TRADEMARK OFFICE
CERTIFICATE OF CORRECTION

PATENT NO. : 6,244,118 B1
DATED : June 12, 2001
INVENTOR(S) : Andersson et al.

Page 1 of 1

It is certified that error appears in the above-identified patent and that said Letters Patent is hereby corrected as shown below:

Column 8, claim 35,
Line 36, "claim 33 or 34" should be -- claim 8 or 34 --.

Signed and Sealed this

Nineteenth Day of February, 2002

Attest:

*Attesting Officer*

JAMES E. ROGAN
*Director of the United States Patent and Trademark Office*